(12) United States Patent
Niehaus et al.

(10) Patent No.: US 7,160,736 B2
(45) Date of Patent: *Jan. 9, 2007

(54) DETECTION AND AMPLIFICATION OF LIGANDS

(75) Inventors: Gary D. Niehaus, Kent, OH (US); Christopher J. Woolverton, Kent, OH (US); Oleg D. Lavrentovich, Kent, OH (US)

(73) Assignee: Kent State University, Kent, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/726,134

(22) Filed: Dec. 1, 2003

(65) Prior Publication Data

US 2004/0175841 A1 Sep. 9, 2004

Related U.S. Application Data

(63) Continuation of application No. 09/821,396, filed on Mar. 29, 2001, now abandoned, which is a continuation-in-part of application No. 09/633,327, filed on Aug. 7, 2000, now abandoned, which is a continuation of application No. 09/095,196, filed on Jun. 10, 1998, now Pat. No. 6,171,802.

(51) Int. Cl.
*G01N 33/553* (2006.01)
*C07H 21/04* (2006.01)

(52) U.S. Cl. .............. 436/525; 435/7.1; 435/5; 435/7.9; 435/7.2; 435/69.1; 436/518; 349/123; 349/124; 349/130; 349/137; 536/23.4; 536/23.5

(58) Field of Classification Search ............. 435/7.1, 435/5, 7.9, 7.2, 69.1, 526, 518; 349/123, 349/124, 130, 137; 530/350; 536/23.4, 536/23.5
See application file for complete search history.

(56) References Cited

U.S. PATENT DOCUMENTS

| 5,252,459 | A | * | 10/1993 | Tarcha et al. | ............ | 435/6 |
| 5,681,571 | A | * | 10/1997 | Holmgren et al. | ....... | 424/236.1 |
| 6,284,197 | B1 | * | 9/2001 | Abbott et al. | ............ | 422/82.05 |
| 6,482,517 | B1 | * | 11/2002 | Anderson | ............. | 428/402.24 |
| 6,524,665 | B1 | * | 2/2003 | Sahouani et al. | ........... | 428/1.2 |

* cited by examiner

Primary Examiner—Long V. Le
Assistant Examiner—Pensee T. Do
(74) Attorney, Agent, or Firm—Hahn Loeser & Parks LLP

(57) ABSTRACT

Devices and systems for the detection of ligands comprising at least one receptor and an amplification mechanism comprising a liquid crystalline, where an amplified signal is produced as a result of receptor binding to a ligand are provided. Also provided are methods for the automatic detection of ligands.

21 Claims, 11 Drawing Sheets

FIG. 4A

 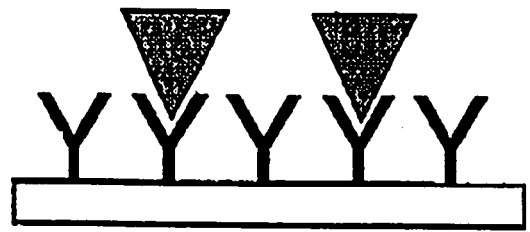
FIG. 6A              FIG. 6B
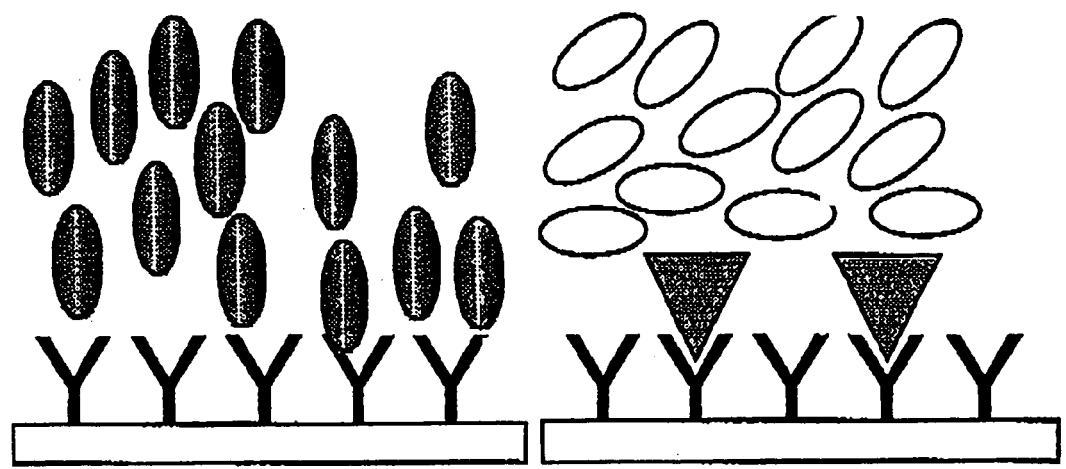
FIG. 7A              FIG. 7B

DETECTION AND AMPLIFICATION OF LIGANDS

CROSS REFERENCE TO RELATED APPLICATIONS

This application is a continuation of application Ser. No. 09/821,396 filed on Mar. 29, 2001, now abandoned which is a continuation-in-part of U.S. Ser. No. 09/633,327, filed Aug. 7, 2000, now abandoned which is a continuation of U.S. Ser. No. 09/095,196, filed Jun. 10, 1998, now U.S. Pat. No. 6,171,802.

TECHNICAL FIELD OF THE INVENTION

The present invention generally relates to the detection of a ligand by a receptor. More specifically, the present invention relates to highly specific receptors and the incorporation of these receptors into an amplification mechanism comprising a liquid crystalline material for the rapid and automatic detection of the ligand, such as microorganisms and products of microorganisms, such as pathogens and/or their toxins.

BACKGROUND OF THE INVENTION

The detection of a ligand by a receptor (for example, detection of a pathogenic agent such as a microbe or toxin by an antibody; or detection of an antibody in blood by another antibody; or binding of a chemical toxin, such as nerve gas, to its receptor) is important in the diagnosis and treatment of individuals exposed to disease-causing agents. Early detection of pathogenic agents can be a great benefit in either disease prophylaxis or therapy before symptoms appear or worsen.

Every species, strain, or toxin of a microbe contains unique internal and external ligands. Using molecular engineering and/or immunological techniques, receptor molecules, such as antibodies, can be isolated that will bind to these ligands with high specificity. Methods have also been developed where receptors, such as antibodies, are linked to a signaling mechanism that is activated upon binding. Heretofore, however, no system has been developed that can automatically detect and amplify a receptor signal coming from the binding of a single or a low number of ligands in near real time conditions. Such a system is imperative for rapid and accurate early detection of ligands.

Many available diagnostic tests are antibody based, and can be used to detect either a disease-causing agent or a biologic product produced by the patient in response to the agent. There are currently three prevailing methods of antibody production for recognition of ligands (antigens): polyclonal antibody production in whole animals with recognition for multiple epitopes, monoclonal antibody production in transformed cell lines with recognition for a single epitope (after screening), and molecularly engineered phage displayed antibody production in bacteria with recognition of a single epitope (after screening). Each of these receptor systems is capable of binding and identifying a ligand, but the sensitivity of each is limited by the particular immunoassay detection system to which it is interfaced.

Immunoassays, such as enzyme-linked immunosorbent assay (ELISA), enzyme immunoassay (EIA), and radioimmunoassay (RIA), are well known for the detection of antigens. The basic principle in many of these assays is that an enzyme-, chromogen-, fluorogen-, or radionucleotide-conjugated antibody permits antigen detection upon antibody binding. In order for this interaction to be detected as a color, fluorescence, or radioactivity change, significant numbers of antibodies must be bound to a correspondingly large number of antigen epitopes.

Thus, there is a need for a system that rapidly, reliably, and automatically detects ligands, especially when present in very small quantities and consequently provides a measurable signal in near real time conditions.

SUMMARY OF THE INVENTION

It is, therefore, an object of the present invention to provide a device, system, and method that will detect a ligand with high sensitivity and high specificity in near real time.

It is another object of the present invention to provide a device, system, and method that will amplify a signal produced by the binding of a ligand to a receptor.

It is a further object of the present invention to provide a device and system that will distort a surrounding liquid crystalline material upon the binding of a ligand to a receptor.

In general, the present invention provides a system for the detection and amplification of ligands, such as pathogenic agents, comprising at least one receptor and an amplification mechanism comprising a liquid crystalline material coupled to that receptor, wherein an amplified signal is produced as a result of the receptor binding the ligand.

In one embodiment, the present invention provides a device for the detection of ligands comprising a plurality of substantially spherical substrates or particles; at least one receptor attached to the spherical particles, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism amplifies said signal upon receptor-ligand complex formation.

In another embodiment, the present invention also provides a method for detecting ligands comprising providing a device capable of detecting ligands, said device comprising a plurality of substantially spherical particles or substrates, at least one receptor attached to the spherical particles, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism comprises a liquid crystalline material and amplifies said signal upon receptor-ligand complex formation; exposing a sample containing at least one ligand to at least one substrate; allowing said receptor to interact with said at least one ligand to form at least one receptor-ligand complex, and measuring the signal generated by said receptor-ligand complex formation.

In another embodiment, the present invention further provides a device for the detection of ligands comprising: at least one substantially spherical substrate coated with a receptor-binding material; at least one receptor attached to said coated spherical substrate, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism amplifies said signal upon receptor-ligand complex formation.

The present invention also provides a method for detecting ligands comprising: providing a device capable of detecting ligands, said device comprising at least one substantially spherical substrate coated with a receptor-binding material; at least one receptor attached to said coated spherical substrate, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism amplifies said signal upon receptor-ligand complex formation; exposing a sample containing at least one ligand to at least one of said substrate; allowing said receptor to interact with said at least one ligand to form at least one receptor-ligand complex; and measuring the signal produced by said receptor-ligand complex formation.

The present invention further provides a device for the detection of ligands comprising: a substantially planar substrate, wherein said substrate is electrically charged; at least one receptor attached to said charged substrate, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism amplifies said signal upon receptor-ligand complex formation.

The present invention further includes a method for detecting ligands comprising: providing a device capable of detecting ligands, said device comprising at least one electrically charged substantially planar substrate; at least one receptor attached to said substrate, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism amplifies said signal upon receptor-ligand complex formation; exposing a sample containing at least one ligand to said substrate; allowing said receptor to interact with said at least one ligand to form at least one receptor-ligand complex; and measuring the signal produced by said receptor-ligand complex formation.

The present invention further provides a device for the detection of ligands comprising: a substantially planar substrate coated with a receptor-binding material; at least one receptor attached to said coated substrate, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism amplifies said signal upon receptor-ligand complex formation.

The present invention also provides a method for detecting ligands comprising: providing a device capable of detecting ligands, said device comprising substantially planar substrate coated with a receptor-binding material; at least one receptor attached to said coated substrate, wherein said at least one receptor is capable of binding to a ligand to form a receptor-ligand complex and wherein the formation of said receptor-ligand complex produces a signal; and an amplification mechanism comprising a liquid crystalline material, wherein said amplification mechanism amplifies said signal upon receptor-ligand complex formation; exposing a sample containing at least one ligand to said substrate; allowing said receptor to interact with said at least one ligand to form at least one receptor-ligand complex; and measuring the signal produced by said receptor-ligand complex formation.

BRIEF DESCRIPTION OF THE DRAWINGS

FIG. 4A is a graph showing the number of light transmissive microdomains in the neutral grey liquid crystalline material using (a) polycarboxylate microspheres coated with anti-*E.coli* antibody and (b) polycarboxylate microspheres coated with Bovine Serum Albumin (BSA). The open circles (○) represent the number of light transmissive microdomains in the neutral grey liquid crystalline material using polycarboxylate microspheres coated with anti-*E.coli* antibody, and the filled in circles (●) represents the number of light transmissive microdomains in the neutral grey liquid crystalline material using polycarboxylate microspheres coated with BSA.

FIG. 6A is a representation of a planar substrate having a plurality of receptors attached to one surface of the substrate and without ligand bound to the receptors.

FIG. 6B is a representation of a substantially planar substrate having a plurality of receptors attached to one surface of the substrate and with some ligands bound to a portion of the receptors.

FIG. 7A is a representation of a planar substrate having a plurality of receptors attached to one surface of the substrate without ligand bound to the receptors showing the liquid crystalline material orientation when ligand is not bound to receptor.

FIG. 7B is a representation of a planar substrate having a plurality of receptors attached to one surface of the substrate with some ligands bound to a portion of the receptors showing the change in liquid crystalline material orientation when ligand is bound to receptor.

DETAILED DESCRIPTION OF THE INVENTION

Figure 1A:
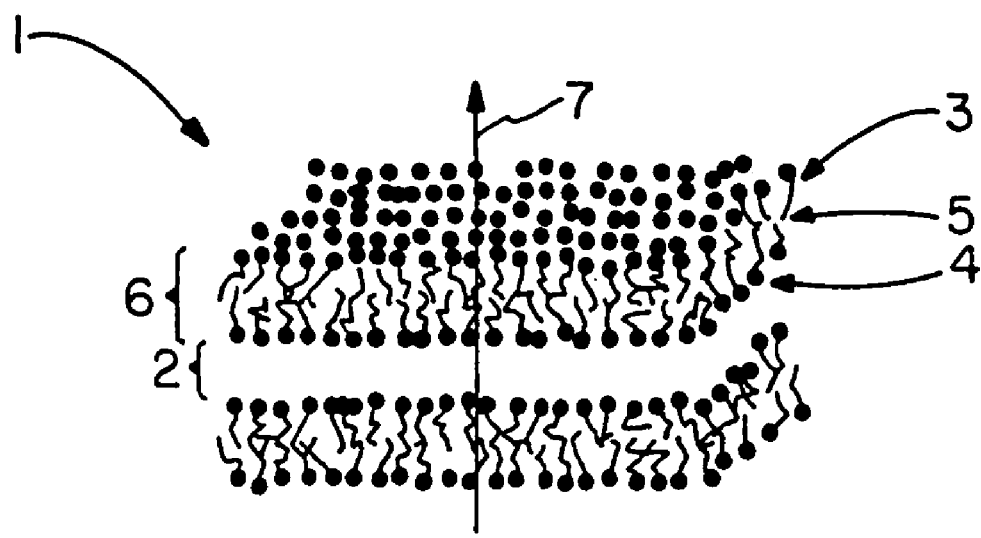
FIG. 1A is a schematic representation of the lamellar structure of a lyotropic liquid crystal formed by alternating layers of water and biphilic molecules.

In the present invention, ligand-specific receptors are interfaced with an amplification mechanism such that a receptor-ligand interaction forms birefringent receptor-ligand aggregates and/or changes the conformation of the receptor and produce a light transmissive signal. Amplification preferably occurs through a birefringent shift that can be photometrically detected. The detected signal may then be electronically amplified to automate the system.

Ligand Dectection Component

Any receptor, such as antibodies or biologic/biologically engineered receptors for ligands, can be incorporated into the device as long as binding of the ligand to the receptor causes a detectable ligand aggregation and/or distortion (change in conformation) of the receptor. For example, any type of monospecific antibody (polyclonal, monoclonal, or phage displayed) can effectively function as a receptor and, thus, each of those antibody types will be described in the following paragraphs. Although phage-displayed antibodies can be expeditiously modified for identification of new ligands and are used as receptor examples in this patent application, any physically-distortable receptor-ligand interaction is appropriate for the detection component.

Polyclonal antibodies: Antibody-based antigen detection has been exploited for several decades. Injection of a purified ligand (antigen) into a host animal stimulates the immune system to produce an array of antibodies against various reactive sites on the antigen. Since several lymphocytes are responding to different antigenic epitopes, a multispecific antibody cocktail (polyclonal) is created and can be purified for antigen detection.

Monoclonal antibodies: Antibody-producing spleen cells (B lymphocytes) are fused with immortalized myeloma cells to create hybridomas which provide nearly infinite quantities of antibody with a single, defined specificity. Interstrain and even interspecies hybrids of these 'monoclonal' antibodies can be generated through genetic engineering techniques. These highly specific antibodies have significant therapeutic potential, as evidenced by the U.S. Food and Drug Administration's approval of the use of mouse-human chimeric antibodies for treatment of selected diseases.

Phage-displayed mono-specific antibodies: Phage-displayed techniques will be used to isolate single chain chimeric antibodies to various pathogenic agents. The genomic DNA of the B lymphocyte contains the code to produce an antibody to virtually all possible ligands (antigens). In a phage displayed antibody system (PDA), DNA encoding a single chain chimera of the native antibody's hypervariable ligand-binding region is synthesized by joining DNA encoding an antibody heavy chain and DNA encoding an antibody light chain and inserting therebetween DNA encoding a linker region. The desired amino acid sequence of the linker region depends on the characteristics required for any given amplification mechanism. The linker region may have to be able to interact and/or bond to a protein or other substance. Therefore, the polypeptide sequence may have to have, for example, a particular conformation, specifically placed functional groups to induce ionic or hydrogen bonds, or a hydrophobicity that is compatible with the amplification mechanism. Regardless of the type of amplification mechanism, however, the linker region plays a critical role in interfacing the amplification mechanism to the receptor.

The DNA, preferably human or mouse, encoding the single chain chimeric antibody is cloned into a bacteriophage (phage) vector using well-known techniques (Marks et al., J. Mol. Bio. Vol. 222:581 (1991); Griffiths et al., EMBO J. 12:725 (1993); and Winters et al., Ann. Rev. Immunol. 12:433 (1994)), incorporated herein by reference. The single chain chimeric antibodies then become displayed on the surface of a filamentous phage with the hypervariable antigen-binding site extended outward.

After the addition of ligands, phage that are reactive against non-targeted ligands are subtracted from the phage library using known techniques (Marks et al., J. Mol. Bio. Vol. 222:581 (1991); Griffiths et al., EMBO. J. 12:725 (1993); and Winters et al., Ann. Rev. Immunol. 12:433 (1994)), incorporated herein by reference. The remaining phage are reacted with their specific ligand and phage reactive with that specific ligand eluted. Each of these phage are then isolated and expressed in a bacterial host, such as *Escherichia coli* (*E.coli*) to produce a large quantity of phage containing the desired surface-displayed antibody.

Each of the aforementioned methods relating to synthesizing and cloning DNA, subtracting phages, isolating and expressing phages and recovering viral DNA are well known and fully described by Marks et al., J. Mol. Biol. (1991); Griffiths et al., EMBO J. 12:725 (1993); and Winters et al., Ann. Rev. Immunol. 12:433 (1994), all of which are incorporated herein by reference.

Amplification Component

An amplification mechanism including liquid crystalline material is utilized to amplify a ligand-receptor complex, thereby detecting the presence of ligands in a sample.

A liquid crystal is a state of matter in which molecules exhibit some orientational order but little positional order. This intermediate ordering places liquid crystals between solids (which possess both positional and orientational order) and isotropic fluids (which exhibit no long-range order). Solid crystal or isotropic fluid can be caused to transition into a liquid crystal by changing temperature (creating a thermotropic liquid crystal) or by using an appropriate diluting solvent to change the concentration of solid crystal (creating a lyotropic liquid crystal). Both thermotropic and lyotropic liquid crystals can be used as the amplification mechanism of the device of the present invention. In one embodiment, chromonic lyotropic liquid crystalline material are used as the amplification component of the device of the present invention.

Among these non-surfactant lyotropic liquid crystals are so-called lyotropic chromonic liquid crystals (LCLCs). The LCLC family embraces a range of dyes, drugs, nucleic acids, antibiotics, carcinogens, and anti-cancer agents. For a review of lyotropic chromonic liquid crystals see J. Lydon, Chromonics, in: Handbook of Liquid Crystals, Wiley-VCH, Weinheim, vol. 2B, p. 981 (1998). The LCLCs are fundamentally different from the better known surfactant-based lyotropic systems. Without limitation, one difference is that LCLC molecules are disc-like or plank-like rather than rod-like. The polar hydrophilic parts form the periphery, while the central core is relatively hydrophobic. This distinction creates a range of different ordered structures. Individual disc-like molecules may form cylindrical aggregates in water. The LCLCs are assumed to be formed by elongated aggregates, lamellar structures, and possibly by aggregates of other shapes.

As seen in FIG. 1A, most lyotropic liquid crystals, designated generally by the numeral 1, are formed using water 2 as a solvent for biphilic molecules 3, for example, molecules which possess polar (hydrophilic) parts 4 and a polar (hydrophobic) parts 5. When water 2 is added to biphilic molecules 3, a bilayer 6 forms as the hydrophobic regions coalesce to minimize interaction with water 2 while enhancing the polar component's interaction with water. The concentration and geometry of the specific molecules define the supramolecular order of the liquid crystal. The molecules can aggregate into lamellae as well as disk-like or rod-like micelles, or, generally, aggregates of anisometric shape. These anisometric aggregates form a nematic, smectic, columnar phase, of either non-chiral or chiral (cholesteric phase) nature. For example, the molecules form a stack of lamellae of alternating layers of water and biphilic molecules, thus giving rise to a lamellar smectic phase.

Lyotropic liquid crystals are usually visualized as ordered phases formed by rod-like molecules in water. A fundamental feature of the surfactant molecules is that the polar hydrophilic head group has an attached flexible hydrophobic tail. There is, however, a variety of other lyotropic systems that are not of the surfactant type, but which can also be successfully used in the present invention.

Liquid crystalline phases are characterized by orientational order of molecules or their aggregates. In the uniaxial liquid crystal phases such as nematic and smectic A, the average direction of orientation of the molecules or aggregates is described by a unit vector, called the director and denoted n. Generally, the two opposite directions of the director are equivalent, n=−n. In the uniaxial phases, the director is simultaneously the optical axis of the medium. An optically uniaxial liquid crystalline medium is birefringent. A uniaxial birefringent medium is characterized by two optical refractive indices: an ordinary refractive index "$n_o$" for an ordinary wave and an extraordinary refractive index "$n_e$" for an extraordinary wave.

When the liquid crystal is viewed between two crossed polarizers, the appearing texture and the intensity of transmitted light are determined by orientation of the optical axis (director) with respect to the polarizers and other factors, as clarified below.

Consider, as an example, a nematic slab sandwiched between two glass plates and placed between two crossed polarizers. We follow the description given by M. Kleman and O. D. Lavrentovich, "Soft Matter Physics: An Introduction," Springer-Verlag New York, (2001). The director n is in plane of the slab and depends on the in-plane coordinates (x,y). We assume that it does not depend on the vertical coordinate z. The light beam impinges normally on the cell, along the axis z. A polarizer placed between the source of light and the sample makes the impinging light linearly polarized. In the nematic, the linearly polarized wave of amplitude A intensity $I_0 = A^2$ and the frequency ω splits into the ordinary and extraordinary waves with mutually perpendicular polarizations and amplitudes A sin β and A cos β, respectively; β is the angle between the local n and the polarization of incident light. The vibrations of the electric vectors at the point of entry are in phase. However, the two waves take different times, $n_o d/c$ and $n_e d/c$, respectively, to pass through the slab. Here d is the thickness of the slab, and c is the speed of light in vacuum. At the exit point, the electric vibrations $$\sim A\sin\beta\cos\left(\omega t - \frac{2\pi}{\lambda_0}n_o d\right) \text{ and } \sim A\cos\beta\cos\left(\omega t - \frac{2\pi}{\lambda_0}n_e d\right)$$

gain a phase shift $$\Delta\varphi = \frac{2\pi d}{\lambda_0}(n_e - n_o),$$

where $\lambda_0$ is the wavelength in vacuum. The projections of these two vibrations onto the polarization direction of the analyzer behind the sample are $$a = A\sin\beta\cos\beta\cos\left(\omega t - \frac{2\pi}{\lambda_0}n_o d\right) \text{ and}$$

$$b = -A\sin\beta\cos\beta\cos\left(\omega t - \frac{2\pi}{\lambda_0}n_e d\right)$$

(Eq. 1)

When two harmonic vibrations $A_1 \cos(\omega t + \phi_1)$ and $A_2 \cos(\omega t + \phi_2)$ of the same frequency occur along the same directions, then the resulting vibration $\overline{A} \cos(\omega t + \overline{\phi})$ has an amplitude defined from $\overline{A}^2 = A_1^2 + A_2^2 + 2A_1 A_2 \cos(\phi_1 - \phi_2)$. The analyzer thus transforms the pattern of (x,y)-dependent phase difference into the pattern of transmitted light intensity $I(x,y) = \overline{A}^2$. The intensity of light passed through the crossed polarizers and the nematic slab between them follows from Eq. (1) as $$I = I_0 \sin^2 2\beta \sin^2 \left[ \frac{\pi d}{\lambda_0} (n_e - n_o) \right]. \quad \text{(Eq. 2)}$$

The last formula refers to the case when n is perpendicular to the axis z. If n makes an angle $\theta$ with the axis z, then (2) becomes $$I = I_0 \sin^2 2\beta \sin^2 \left[ \frac{\pi d}{\lambda_0} \left( \frac{n_o n_e}{\sqrt{n_e^2 \cos^2 \theta + n_o^2 \sin^2 \theta}} - n_o \right) \right] \quad \text{(Eq. 3)}$$

Below is a representation of the propagation of light through a polarizer, uniaxial slab and analyzer.

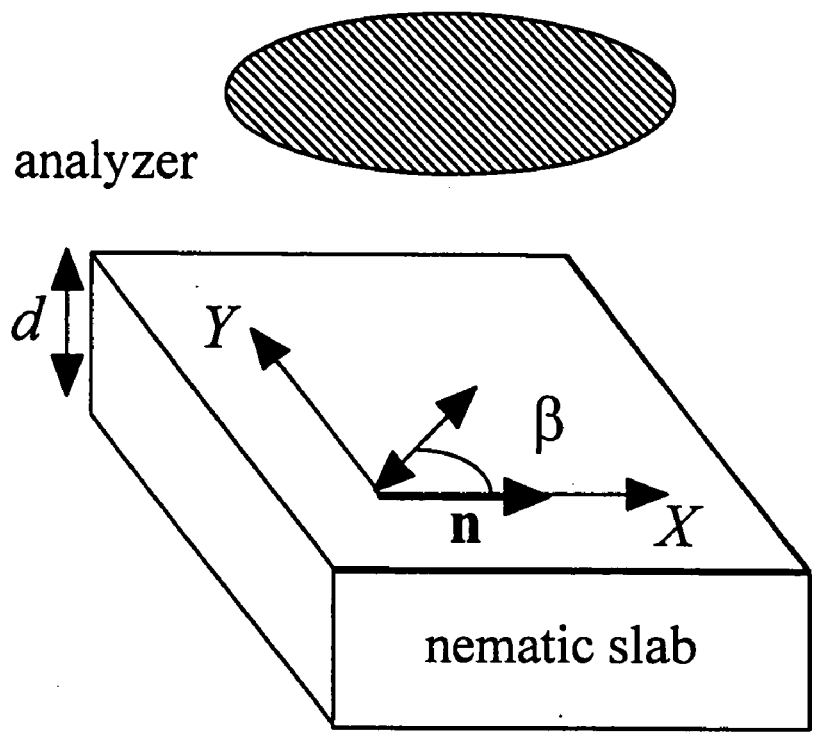
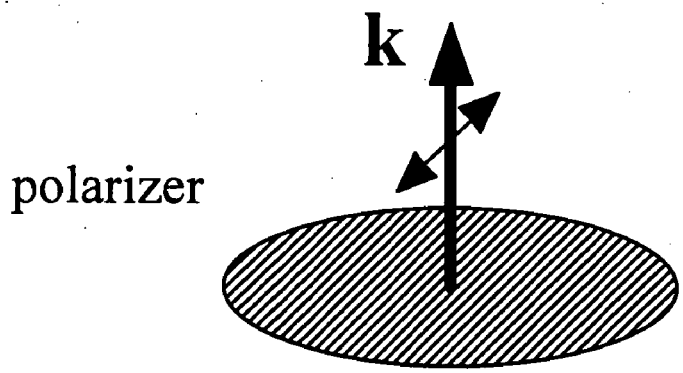

The treatment can be further extended to describe the optical properties of complex director configurations, for example, in the electric field-driven cells. However, for the case when the director is distorted by ligand-receptor interactions rather than by an externally applied electric or magnetic field equations (2) and (3) are fundamental for understanding liquid crystal textures. First, note that the phase shift and thus I depend on $\lambda_0$. As a result, when the sample is illuminated with a white light, it would show a colorful texture. The interference colors are especially pronounced when $(n_e-n_o)d\sim(1\div3)\lambda_0$. With typical $(n_e-n_o)\sim0.2$, $\lambda_0\sim500$ nm, the 'colorful' range of thicknesses is $d\sim(1\div10)$ μm. Second, the director tilt θ greatly changes the phase shift. When n∥z (the so-called homeotropic orientation, θ=0, the sample looks dark: only the ordinary wave propagates and, according to Eq. (3), I=0. Third, if θ=0 but β=0, π/2, . . . , one might still observe dark textures, I=0, even in non-monochromatic light. In a sample with in-plane director distortions n(x,y), wherever n (or its horizontal projection) is parallel or perpendicular to the polarizer, the propagating mode is either pure extraordinary or pure ordinary and the corresponding region of the texture appears dark. By aligning a well-oriented liquid crystal sample between two crossed polarizers, one can find an "extinction" position in which the sample is dark. This extinction position corresponds to the director aligned along the polarization direction of polarizer or analyzer, β=0, π/2, . . . , .

The extinction state will occur for all points of the sample, as long as the director field is not perturbed and uniform. However, if the director field is disturbed and varies from point to point within the slab, then the condition of extinction (meaning I=0 in Equations (2) and (3)) cannot be satisfied everywhere and the resulting intensity of light passing through the polarizer, liquid crystal slab and analyser will be different from zero. Such a disturbance of the liquid crystal detector can be caused by the receptor-ligand interaction, if this interaction realigns the liquid crystalline molecules or aggregates in the neighborhood. These are the important features allowing us to use the liquid crystals as detection and amplification system.

Most biologic receptors possess both hydrophilic and hydrophobic regions and, thus, readily incorporate into biphilic lyotropic liquid crystals. Additionally, the inactivated receptors do not destroy the optical anisotropy (birefringence) of the liquid crystal and, therefore, the device comprised of a receptor-enriched liquid crystal with a following analyzer remains nontransparent to polarized light when proper alignment satisfies the condition of extinction, as seen from equations (2) and (3). In this case, light would be able to pass through the liquid crystal but the analyzer would not let light pass any further, because the polarization of the light will be perpendicular to the plane of polarization of the analyzer. However, director orientation and, thus, the orientation of optical axis is disrupted when receptor conformation shifts as during the formation of the receptor-ligand complex. The elasticity of the liquid crystal enhances the local distortions in the vicinity of the receptor-ligand complex, and expands it to an optically detectable, supramicron scale. These distortions generally deviate the director from the "extinction" orientations such as β=0, ±π2, . . . , and make the system locally transparent, as the light beam is not blocked by the analyzer.

Configurations of Ligand Detection Device

By way of example, one envisioned application of the present invention is in a multiwell system. Each well of the system would contain PDAs to a specific ligand, such as a pathogenic microbe, interfaced with an amplification mechanism of the present invention. When the microbial agent interacts with the antibody, the resulting antibody distortion triggers the amplification mechanism. Preferably, the amplified signal is then transduced into a perceptible signal. Accordingly, it is envisioned that such a system could be placed in a physician's office, and be used in routine diagnostic procedures. Alternatively, such a system could be placed on or near soldiers in battle, and the invention used to alert the soldiers to the presence of a toxic agent. It is further envisioned that a multiwell system, is preferably used in conjunction with the liquid crystal embodiment described herein.

Figure 1B:
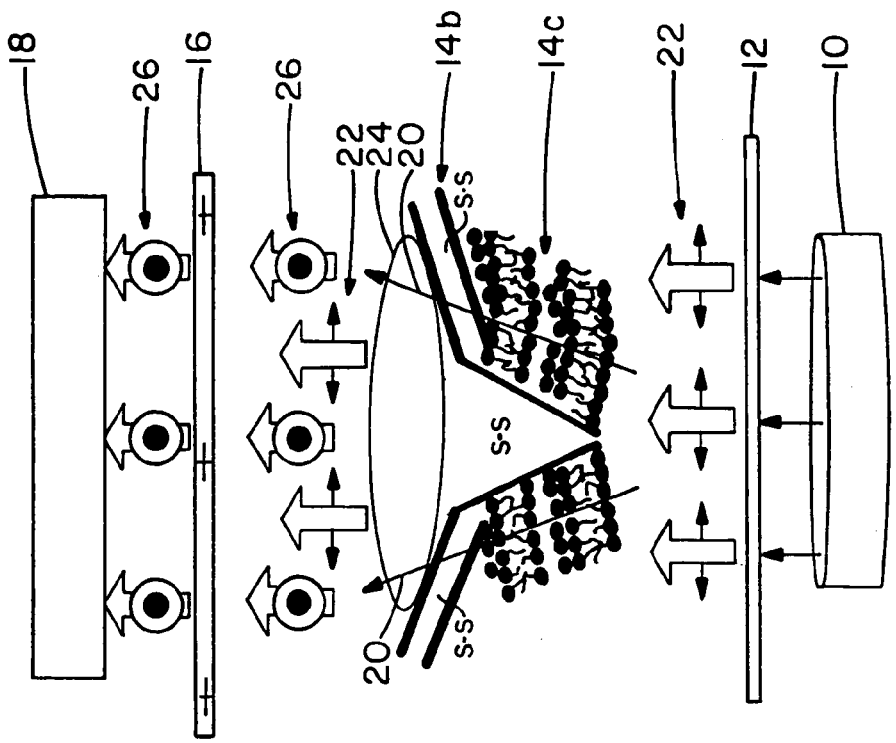
FIG. 1B is a schematic representation of the amplification mechanism with a receptor inserted into the lyotropic liquid crystal.
Figure 1C:
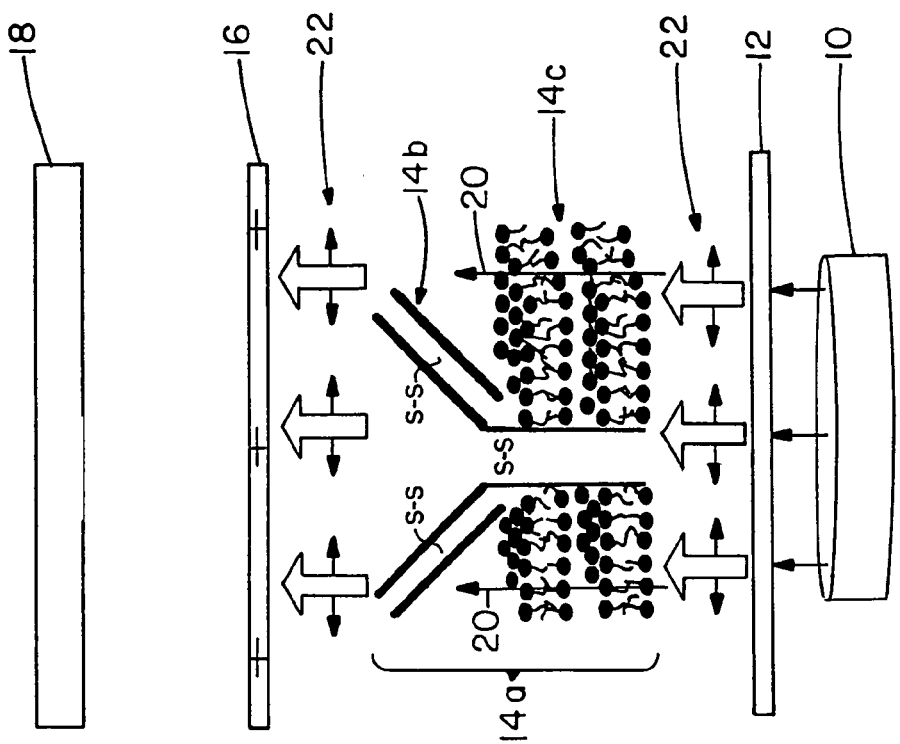
FIG. 1C is a schematic representation of the amplification mechanism with the specific ligand bound to its receptor causing deformation of the liquid crystal and alteration of the transmission of polarized light.
Figure 2A:
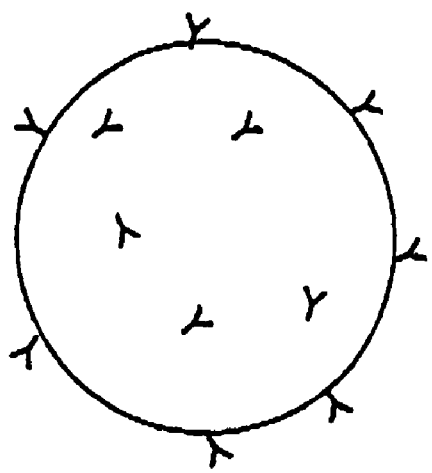
FIG. 2A is a representation of a non-porous (solid) spherical particle or substrate having a plurality of receptors attached to the outer surface of the sphere.
Figure 2B:
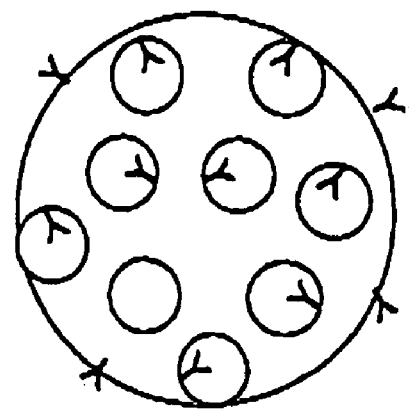
FIG. 2B is a representation of a porous spherical particle or substrate having a plurality of receptors attached to the outer surface of the sphere and within the pores of the sphere.
Figures 2C, 2D:
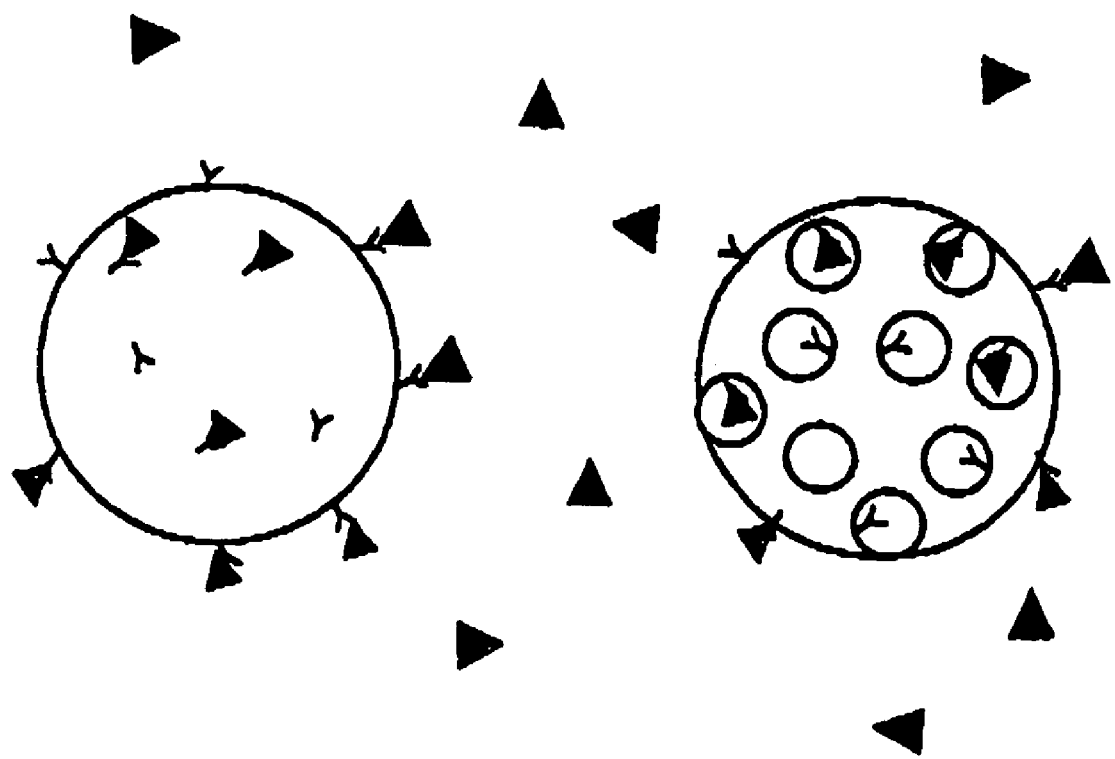
FIG. 2C is a representation of a non-porous (solid) spherical particle or substrate having a plurality of receptors attached to the outer surface of the sphere with ligand bound to a portion of the receptors.
FIG. 2D is a representation of a porous spherical particle or substrate having a plurality of receptors attached to the outer surface of the sphere and within the pores of the sphere with ligand bound to a portion of the receptors.
Figures 3A, 3B:
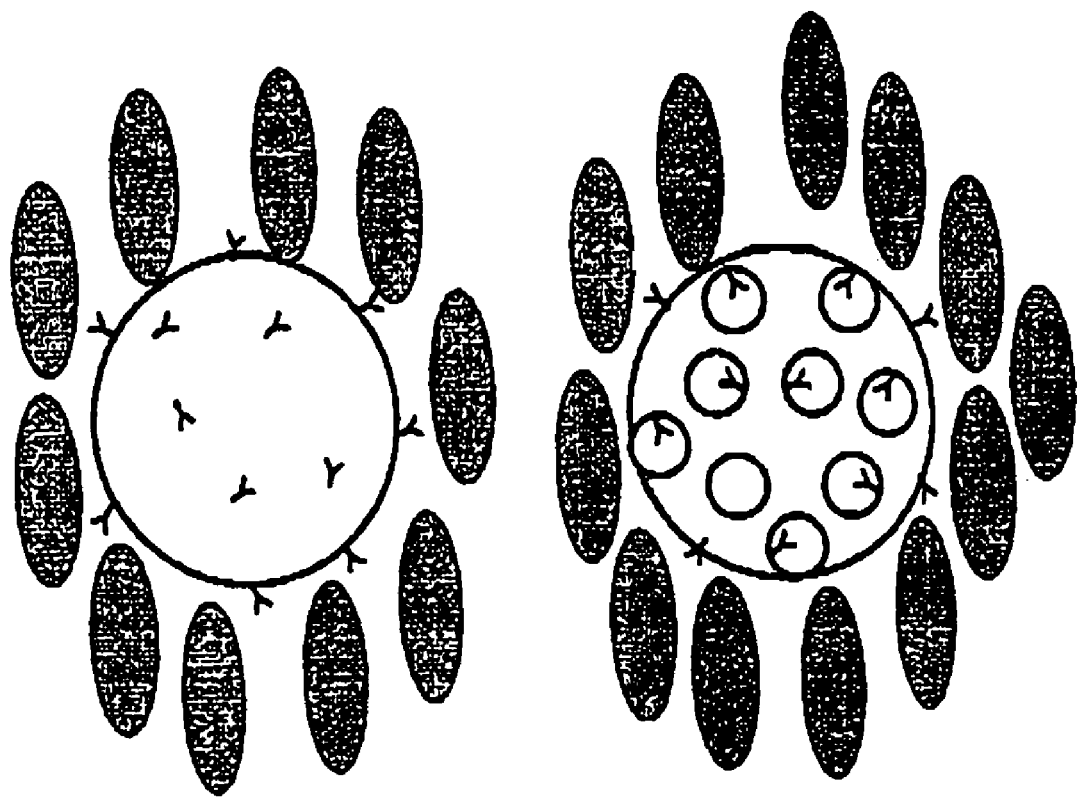
FIG. 3A is a representation of, a non-porous (solid) spherical particle or substrate having a plurality of receptors attached to the outer surface of the sphere showing the liquid crystalline material orientation about the receptor-bound sphere.
FIG. 3B is a representation of, a porous spherical particle or substrate having a plurality of receptors attached to the outer surface of the sphere and within the pores of the sphere showing the liquid crystalline material orientation about the receptor-bound sphere.
Figure 3C:
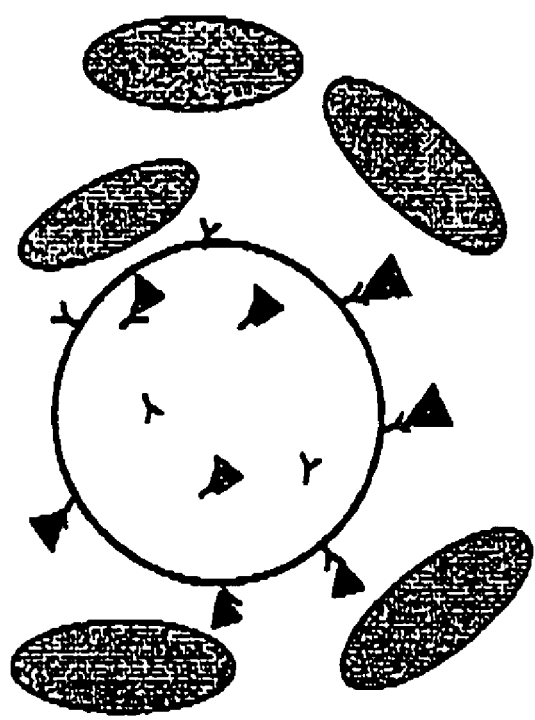
FIG. 3C is a representation of a non-porous (solid) spherical particle or substrate having a plurality of receptors attached to the outer surface of the sphere with ligand bound to a portion of the receptors showing the change in liquid crystalline material orientation about the sphere when ligand is bound.
Figure 3D:
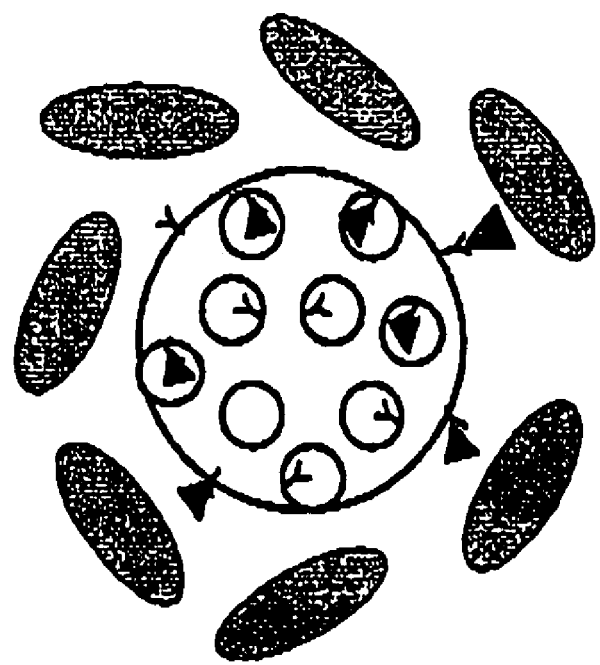
FIG. 3D is a representation of a porous spherical particle or substrate having a plurality of receptors attached to the outer surface of the sphere and within the pores of the sphere with ligand bound to a portion of the receptors showing the change in liquid crystalline material orientation about the sphere when ligand is bound.

Thus, in one embodiment of the present invention, shown schematically in FIGS. 1B and 1C, a lyotropic liquid crystalline material is used as an amplification mechanism. As shown in FIG. 1B, the device consists of a light source 10, an initial polarizer 12, with the direction of polarization in the plane of the figure, a pathogen detection system 14a, comprising monospecific antibodies 14b embedded in biphilic, lyotropic liquid crystalline material 14c, a secondary polarizer 16, with the direction of polarization perpendicular to the plane of the figure, and a photodetector 18.

In operation, the initial polarizer 12 organizes a light beam 22 that is linearly polarized in the plane of the figure. The optical axis 20 of the inactivated device is perpendicular to the pathogen detection system 14a, and thus no birefringence of the transluminating linearly polarized light stream 22 occurs. Since the polarization direction of the secondary polarizer 16 is perpendicular to the transluminating linearly polarized light 22, the secondary polarizer prevents light from reaching the photodetector 18.

Binding of a ligand 24, such as a microbe, to the receptor 14b, such as an antibody, distorts the liquid crystal 14c, and thus causes detectable changes in the light transmitted through the sample between two crossed polarizers. This activation process is illustrated in FIG. 1C. The receptor (antibody) 14b is embedded in the lyotropic liquid crystal 14c. The spacial distortion caused by the formation of the antigen-antibody complex is transmitted to the contiguous liquid crystal 14c. The elastic characteristics of the liquid crystal permit the distortion to be transmitted over a region much larger than the size of the receptor-ligand complex. This allows the use of the standard optical phenomenon of birefringence to detect distortions caused by the receptor-ligand complex, see Max Born and E. Wolf., Principals of Optics, Sixth edition, Pressman Press, Oxford, 1980), as well as the discussion above. The altered liquid crystalline order distorts the optical axis 20 and induces changes in the transmitted light, as discussed above. For example, if the sample is originally aligned in the 'extinction" position (so that β=0 or β=π/2), the transmission of light through the two crossed polarizers and a sample between them is zero. The distortions caused by the receptor-ligand complex violate the condition of complete extinction since these distortions deviate the angle β from the values β=0 and/or β=π/2. Therefore, the transmittance of the light through the pair of polarizers and the liquid crystal sample will be different from zero in the regions of sample where the distortions occur. The secondary polarizer (analyzer) 16 allows this portion of light to pass to the photodetector 18. The detected change or amplification in light intensity can be transduced electronically into a perceptible signal.

In one preferred embodiment, the device of the present invention may include a plurality of substantially spherical particles or substrates to which receptors may be attached.

The receptor or receptors that are attached to the spherical particles must be capable of binding to a desired ligand to form a receptor-ligand complex such that, upon formation of said receptor-ligand complex a signal is produced. An amplification mechanism is interfaced with the receptor-ligand complex, where the amplification mechanism amplifies the signal produced by receptor-ligand complex formation.

The particles utilized in the present invention can be non-porous (solid) or porous. In one embodiment, the substantially spherical substrate is a solid sphere and the at least one receptor is attached to the outer surface of the spherical particles.

In another embodiment, the particles are porous. According to this embodiment, the at least one receptor may be attached to either the surface of the particle, the pores of the porous particles, or both. By way of non-limiting example, if only one receptor is attached to the particle, then the receptor can be attached to either the outer surface of the porous sphere or in the pores of the sphere. In embodiment having more than one receptor attached to the particle, then the receptors can all be attached to the outer surface of the sphere, all the receptor can be attached within the pores of the sphere, or some receptors can be attached to the outer surface of the sphere and other receptors can be attached to the pores of the sphere. The use of a particle such as a porous sphere or bead provides a greater surface area on which to attach receptors and, therefore, would also permit surface and luminal receptor-ligand interactions.

The receptors may be attached to the particle in any manner known in the art, including chemical attachment and physical attachment. In one preferred embodiment, the receptors are attached to the particle by a chemical attachment, such as by covalent bonding to sulfate, amine, carboxyl or hydroxyl groups imbedded in the particle. However, it should be noted that the receptors wherein said at least one receptor is attached to the particle by any means of physical attachment.

The particles may be made from a material including, but not limited to, polymeric and inorganic materials. In one preferred embodiment, the substantially receptor-coated spherical substrate is comprised of a polymeric material. Suitable polymeric materials which may comprise the spherical substrate include, but are not limited to, polyalkenes, polyacrylates, polymethacrylates, polyvinyls, polystyrenes, polycarbonates, polyesters, polyurethanes, polyamides, polyimides, polysulfones, polysiloxanes, polysilanes, polyethers, polycations, polyanions, and polycarboxylates. One particularly useful polymeric material used to manufacture the spherical substrate is polystyrene, especially when modified with copolymers of acrylic ester, chloromethylstyrene, methylolamine, methyl methacrylate or made zwitterionic. If a polycation is utilized as the material of the spherical substrate, one particularly suitable polycation is poly(diallyldimethylammoniumchloride).

In another embodiment, the particles may be made from an inorganic material. Suitable inorganic materials include, but are not limited to, glass, silicon, and colloidal gold. In one preferred embodiment, the spherical substrate is a glass bead.

The liquid crystalline material that is utilized with the particles includes all known types of thermotropic liquid crystalline materials and lyotropic liquid crystalline materials. In one preferred embodiment, lyotropic liquid crystalline material is used as the amplification mechanism. In another embodiment, lyotropic liquid crystalline materials of different origin, including surfactant and lyotropic chromonic liquid crystalline material, may used with the spherical particles.

As described herein above, any receptor, such as antibodies or biologic/biologically engineered receptors for ligands, can be incorporated into the device as long as binding of the ligand to the receptor produces a detectable signal. Therefore, any type of monospecific antibody, including all polyclonal, monoclonal, or phage displayed antibodies can effectively function as a receptor.

In another embodiment, the present invention provides a method for detecting ligands. The method for detecting ligands, according this embodiment, includes providing a device that comprises a plurality of particles, at least one receptor attached to each of the plurality of particles, and an amplification mechanism. The at least one receptor must be capable of binding to a ligand to form a receptor-ligand complex and, upon formation of the receptor-ligand complex, a signal is produced. The amplification mechanism must be capable of amplifying the signal produced by the receptor-ligand complex formation. Generally, a sample containing ligands specific to the receptor that is attached to the particles is exposed to the device. After exposing the ligand-containing sample to the device, the receptor or plurality of receptors that are attached to each of the plurality of particles are allowed to interact with the ligands in the sample to form at least one receptor-ligand complex. The formation of the receptor-ligand complex produces a detectable signal. The signal generated by the formation of the receptor-ligand complex is amplified by the amplification mechanism, namely, the liquid crystalline material. The amplified signal may then be measured and quantitated by those known methods easily determined by those having ordinary skill in the art.

In one embodiment, the measurement and quantitation of the of the receptor-ligand complex formation is mediated in the fluid phase or "flow through" phase, whereby the spheres and the liquid crystalline material are injected through an optical device that can determine the orientation of the liquid crystalline material. Utilizing this particular method of quantitation permits "field capture" of ligands using previously prepared spherical beads having a predetermined receptor attached thereto. Thus, for example, the ligands can be captured "in the field",transported, and analyzed at the later time. This method obviates the need for special transport media usually required to "protect" the ligand until detection is performed.

In another embodiment, the device for the detection of ligands comprises a plurality of particles or substrates coated with a receptor-binding or receptor-crosslinking material, at least one receptor attached to the coated particle, and an amplification mechanism comprising a liquid crystalline material. The at least one receptor is capable of binding to a ligand to form a receptor-ligand complex and the formation of the receptor-ligand complex produces a signal. The signal produced is then amplified by the amplification mechanism upon receptor-ligand complex formation. According to the present embodiment, the crosslinker material may be, without limitation, natural or synthetic polymers, proteins, and secondary antibodies.

In one preferred embodiment, molecules with specificity for receptors, such as the specificity exhibited by Protein A, Protein G or anti-immunoglobulin antibodies for immunoglobulins, will be chemically cross linked to the spherical particles. Receptors with specificity for unique pathogens, toxins or proteins will then be bound to the immobilized molecules.

In another embodiment, the present invention provides a method for detecting ligands comprising providing a device capable of detecting ligands. According to this embodiment, the device comprises a plurality of particles coated with a receptor-binding material; at least one receptor attached to the particles, and an amplification mechanism comprising a liquid crystalline material. The at least one receptor is capable of binding to a ligand to form a receptor-ligand complex and upon the formation of a receptor-ligand complex produces a signal. The amplification mechanism amplifies said signal upon receptor-ligand complex formation. The method includes exposing a sample containing at least one ligand to at least one of said substrate and allowing the receptor to interact with the ligands in the sample to form at least one receptor-ligand complex. The signal produced by said receptor-ligand complex formation is then measured.

In another preferred embodiment, the device for detecting ligands comprises an electrically charged, substantially planar substrate, at least one receptor attached or bound to the planar substrate, and an amplification mechanism including a liquid crystalline material.

As described above the spherical substrates, the liquid crystalline material that is utilized with the substantially coated spherical substrate includes all known types of thermotropic liquid crystalline materials and lyotropic liquid crystalline materials. In a preferred embodiment, lyotropic liquid crystalline materials are used with the electrically charged substrate. In another preferred embodiment, lyotropic chromonic liquid crystalline material is utilized.

In another embodiment, a method for detecting ligands is disclosed comprising providing a device capable of detecting ligands, the device comprising at least one electrically charge substantially planar substrate, at least one receptor attached to the substrate, and an amplification mechanism comprising a liquid crystalline material. The at least one receptor is capable of binding to a ligand to form a receptor-ligand complex and the formation of a receptor-ligand complex produces a signal. A sample containing ligands is exposed to the receptor coated substrate, and is allowed to interact with the receptors to form at least one receptor-ligand complex. The signal produced by the receptor-ligand complex formation is amplified by the liquid crystalline amplification mechanism.

The present invention also provides a device for the detection of ligands including an electrically charged, substantially planar substrate, at least one receptor and an amplification mechanism. The at least one receptor attached to the charged substrate is capable of binding to a ligand to form a receptor-ligand complex. The formation of the receptor-ligand complex produces a detectable signal, which is amplified by the amplification mechanism comprising a liquid crystalline material.

A charged substrate may be formed by depositing a polyionic material from an aqueous solution onto the substrate. Without limitation, for example, poly(diallyldimethylammoniumchloride) becomes positively charged in aqueous solutions as negatively charged C1 atoms dissociate from the molecule. To deposit the polyion layer onto a glass substrate, the substrate should be cleaned and then dipped it into the aqueous solution of the polyion. The polyion adsorbs to the surface of the substrate. The excess of the polyion can be washed out with an aqueous solution. In one preferred embodiment, an electrically charged shperical substrate is utilized with lyotropic chromonic liquid crystals. According to this embodiment, the opposite electric charges of the polyionic substrate and the chromonic liquid crystalline molecules are kept in close contact by electrostatic forces.

In another embodiment, the present invention further provides a device for the detection of ligands comprising an substantially planar substrate coated with a receptor-binding or crosslinking material, at least one receptor, and an amplification mechanism. The at least one receptor attached to the coated substrate is capable of binding to a ligand to form a receptor-ligand complex. The formation of the receptor-ligand complex produces a signal, which is amplified by the amplification mechanism comprising a liquid crystalline material. As described above for spherical substrates, the planar substrate is coated with molecules having specificity for receptors that include, without limitation, polymers, Protein A, Protein G, anti-immunoglobulin antibodies for immunoglobulins. Receptors with specificity for unique pathogens, toxins, or proteins will then be bound to the immobilized receptor-binding or crosslinker molecules coated on the surface of the substrate.

In a variation of the is embodiment, the coated substantially planar substrate may also be electrically charged by any suitable means.

In one preferred embodiment, when utilizing any of the above described ligand detection and amplification devices, the non-specific aggregates are removed from the ligand containing sample prior to reacting the ligands with receptor and measuring the signal produced. The non-specific aggregates may be removed by any suitable means including, but not limited to, filtering. The filtered sample will then be reacted with the desired receptor and the resulting signal produced by the formation of receptor-ligand complex will be amplified by the liquid crystalline material and measured. Without being bound to any particular theory, it is thought that the presence of the large non-specific aggregates will increase light transmission through the liquid crystalline material and may, therefore, produce false positive signals.

EXAMPLES

The following examples demonstrate the use of one embodiment of the present invention, namely, substantially receptor-coated microspheres with the liquid crystal amplification mechanism to detect and amplify ligands upon receptor-ligand complex formation. A ligand detection system was created by introducing into the liquid crystal amplification mechanism a desired quantity of microspheres whose surface was substantially coated with microbe-specific antibodies. The examples are intended for illustrative purposes only, and should not be construed as limiting the scope of the present invention in any manner.

The devices were evaluated by inserting antibody-coated microspheres into a lyotropic liquid crystal. For each assay, 10 μl of serially diluted microspheres (coated with either the anti-$E.$ $coli$ K99 antibody or BSA) was mixed with 10 μl of the stock $E.$ $coli$ solution and incubated for 30 minutes at room temperature. The 20% stock solution of liquid crystal (50 μl) was added to the microsphere-antibody solution and gently mixed prevent the formation of bubbles. A 60 μl fraction of the mixture was deposited on a clean, polymer-coated glass square (1 mm thick; 25 mm square). A second cleaned, polymer-coated glass square was aligned with the first square and pressure applied to uniformly distribute the sample. A sample depth of approximately 20 μm was maintained by mylar spacers located between the two glass squares. The edges of the glass assay chambers were sealed with nail polish.

Liquid crystals are anisometric molecules that exhibit limited chemical interaction but that tend to orient along a common direction (the director). Director orientation is affected by externally applied fields (electrical and magnetic); at the boundary between the liquid crystal and it's container and flow. The liquid crystal orientation was optimized by constructing glass assay chambers that enhanced container-liquid crystal interaction. The chambers were created as follows: Borosilicate glass (1.0 mm thick; 200 mm×200 mm) plates were cleaned for 5 minutes in an 60° C. ultrasonic bath containing Alconox Detergent (Fisher Scientific; Hanover Park, Ill. product # 04-322-4) in water, rinsed in distilled water and dried at 100° C. Each plate was coated with an aligned layer of a polymer. The glass plate was cut into 25 mm squares. A 25 mm square was positioned polymer up with two mylar spacer strips (20 µm thick, 2.0 mm×25 mm) located on the outer edges of the glass parallel to the orientation of the polymer. Liquid crystal-microsphere samples (60 µl) were applied at the bottom edge of the glass between the mylar strips and a second 25 mm polymer-coated glass was positioned so that it's polymer orientation was parallel to the bottom glass. Pressure was applied to the top glass to distribute the sample. The edges were sealed with an appropriate sealing material.

Two liquid crystal solutions were evaluated. Lyotropic liquid crystals were formed when either 20% disodium cromoglycate (Hartshorne and Woodard, *Mol. Cryst. Liq. Cryst.* 23:343, 1973) or 20% neutral grey was added to 80% distilled water (w/v). Preliminary phase diagrams demonstrate that both the disodium cromoglycate (Sigma Chem. Co, St. Louis, Mo. product # C0399) and the neutral grey (Optiva Inc., San Francisco, Calif.) liquid crystalline solutions remained in nematic phase at 24° C. when diluted to a 14% solution.

For Examples 1–8, cultures of *E. coli* (ATCC number 23503), grown to mid log growth phase in tryptic soy broth (Becton Dickinson, Sparks, Md. product # 211822), were washed free of growth medium with two washes of Phosphate Buffered Saline were used. The optical density of each *E. coli* suspension at 600 nm was measured and the bacteria concentration extrapolated from a growth curve (optical density at 600 nm versus colony-forming units (CFUs)). Bacteria were then diluted with sterile phosphate buffered saline (PBS) to a concentration of $10^8$ CFU per 10 µl.

Each mixture was evaluated for light transmissive zones at 200× magnification using a microscope equipped with crossed polarizers. For each assay cassette, the number of light transmissive zones in ten microscope fields were counted and the mean number per field calculated. Each experiment was conducted in duplicate. The data points in each of the following graphs represent the mean of the duplicate experiments.

Example 1

A commercially available 1.0 µm diameter polystyrene microsphere was obtained (Polysciences, Inc, Warrington, Pa.). The polystyrene microsphere was coated with a protein that tightly binds microbe specific antibodies. Protein G, a *S. aureus* protein that binds the Fc fraction of immunoglobulins, was cross-linked to the outer surface of the polystyrene microspheres.

A commercially available murine antibody (Accurate Chemical Co.; Westbury, N.Y. product # YCC-311-603) specific to the sex pili (K99) of *E. coli* bacteria was obtained and used undiluted. A stock solution of assay microspheres ($10^7$/µl) was created by incubating 44 µl of microspheres with 56 µl of the murine anti-*E. coli* antibody for 30 minutes at room temperature. The solution was washed twice with phosphate buffered saline to remove unbound primary antibody.

10 µl of serially diluted polystyrene microspheres coated with the anti-*E. coli* K99 antibody was mixed with 10 µl of the stock *E. coli* solution and incubated for 30 minutes at room temperature. The 20% stock solution of neutral grey liquid crystal (50 µl) was added to the microsphere-antibody solution, mixed, and the samples gently centrifuged (3500 g; 5 sec.) to eliminate bubbles. A 60 µl fraction of the mixture was introduced into the glass assay chamber described above.

Comparative Example 2

A commercially available 1.0 µm diameter polystyrene microsphere was obtained (Polysciences, Inc, Warrington, Pa.). The polystyrene microsphere was coated with a protein that tightly binds microbe specific antibodies. Protein G, a *S. aureus* protein that binds the Fc fraction of immunoglobulins, was cross-linked to the outer surface of the polystyrene microspheres.

A stock solution of assay microspheres ($10^7$/µl) was created by incubating 44 µl of microspheres with 56 µl BSA for 30 minutes at room temperature. The solution was washed twice with phosphate buffered saline to remove unbound primary antibody.

10 µl of serially diluted polystyrene microspheres coated with BSA was mixed with 10 µl of the stock *E. coli* solution and incubated for 30 minutes at room temperature. The 20% stock solution of the neutral grey liquid crystal (50 µl) was added to the microsphere-antibody solution, mixed, and the samples gently centrifuged (3500 g; 5 sec.) to eliminate bubbles. A 60 µl fraction of the mixture was introduced into the glass assay chamber described above.

Example 3

A commercially available 1.0 µm diameter polycarboxylate microsphere was obtained (Polysciences, Inc, Warrington, Pa.). The polycarboxylate microsphere was coated with a protein that tightly binds microbe specific antibodies. The polycarboxylate microsphere was coated with a goat immunoglobulin that binds all mouse immunoglobulins.

As described in Example 1 above, a commercially available murine antibody specific to the sex pili (K99) of *E. coli* bacteria was obtained and used undiluted. A stock solution of assay microspheres ($10^7$/µl) was created by incubating 44 µl of microspheres with 56 µl of the murine anti-*E. coli* antibody for 30 minutes at room temperature. The solution was washed twice with phosphate buffered saline to remove unbound primary antibody.

10 µl of serially diluted polycarboxylate microspheres coated with the anti-*E. coli* K99 antibody was mixed with 10 µl of the stock *E. coli* solution and incubated for 30 minutes at room temperature. The 20% stock solution of neutral grey liquid crystal (50 µl) was added to the microsphere-antibody solution, mixed, and the samples gently centrifuged (3500 g; 5 sec.) to eliminate bubbles. A 60 µl fraction of the mixture was introduced into the glass assay chamber described above.

Comparative Example 4

A commercially available 1.0 µm diameter polycarboxylate microsphere was obtained (Polysciences, Inc, Warrington, Pa.). The polycarboxylate microsphere was coated with a protein that tightly binds microbe specific antibodies. The polycarboxylate microsphere was coated with a goat immunoglobulin that binds all mouse immunoglobulins.

A stock solution of assay microspheres ($10^7/\mu l$) was created by incubating 44 μl of microspheres with 56 μl of BSA for 30 minutes at room temperature. The solution was washed twice with phosphate buffered saline to remove unbound primary antibody.

10 μl of serially diluted polycarboxylate microspheres coated with BSA was mixed with 10 μl of the stock $E.$ $coli$ solution and incubated for 30 minutes at room temperature. The 20% stock solution of the neutral grey liquid crystal (50 μl) was added to the microsphere-antibody solution, mixed, and the samples gently centrifuged (3500 g; 5 sec.) to eliminate bubbles. A 60 μl fraction of the mixture was introduced into the glass assay chamber described above.

Example 5

A commercially available 1.0 μm diameter polystyrene microsphere was obtained (Polysciences, Inc, Warrington, Pa.). The polystyrene microsphere was coated with a protein that tightly binds microbe specific antibodies. Protein G, a $S.$ $aureus$ protein that binds the Fc fraction of immunoglobulins, was cross-linked to the outer surface of the polystyrene microspheres.

A commercially available murine antibody (Accurate Chemical Co.; Westbury, N.Y.; product # YCC-311-603) specific to the sex pili (K99) of $E.$ $coli$ bacteria was obtained and used undiluted. A stock solution of assay microspheres ($10^7/\mu l$) was created by incubating 44 μl of microspheres with 56 μl of the murine anti-$E.$ $coli$ antibody for 30 minutes at room temperature. The solution was washed twice with phosphate buffered saline to remove unbound primary antibody.

10 μl of serially diluted polystyrene microspheres coated with the anti-$E.$ $coli$ K99 antibody was mixed with 10 μl of the stock $E.$ $coli$ solution and incubated for 30 minutes at room temperature. The 20% stock solution of disodium cromoglycate liquid crystal (50 μl) was added to the microsphere-antibody solution, mixed, and the samples gently centrifuged (3500 g; 5 sec.) to eliminate bubbles. A 60 μl fraction of the mixture was introduced into the glass assay chamber described above.

Comparative Example 6

A commercially available 1.0 μm diameter polystyrene microsphere was obtained (Polysciences, Inc, Warrington, Pa.). The polystyrene microsphere was coated with a protein that tightly binds microbe specific antibodies. Protein G, a $S.$ $aureus$ protein that binds the Fc fraction of immunoglobulins, was cross-linked to the outer surface of the polystyrene microspheres.

A stock solution of assay microspheres ($10^7/\mu l$) was created by incubating 44 μl of microspheres with 56 μl BSA for 30 minutes at room temperature. The solution was washed twice with phosphate buffered saline to remove unbound primary antibody.

10 μl of serially diluted polystyrene microspheres coated with BSA was mixed with 10 μl of the stock $E.$ $coli$ solution and incubated for 30 minutes at room temperature. The 20% stock solution of the disodium cromoglycate liquid crystal (50 μl) was added to the microsphere-antibody solution, mixed, and the samples gently centrifuged (3500 g; 5 sec.) to eliminate bubbles. A 60 μl fraction of the mixture was introduced into the glass assay chamber described above.

Example 7

A commercially available 1.0 μm diameter polycarboxylate microsphere was obtained (Polysciences, Inc, Warrington, Pa.). The polycarboxylate microsphere was coated with a protein that tightly binds microbe specific antibodies. The polycarboxylate microsphere was coated with a goat immunoglobulin that binds all mouse immunoglobulins.

As described in Example 1 above, a commercially available murine antibody specific to the sex pili (K99) of $E.$ $coli$ bacteria was obtained and used undiluted. A stock solution of assay microspheres ($10^7/\mu l$) was created by incubating 44 μl of microspheres with 56 μl of the murine anti-$E.$ $coli$ antibody for 30 minutes at room temperature. The solution was washed twice with phosphate buffered saline to remove unbound primary antibody.

10 μof serially diluted polycarboxylate microspheres coated with the anti-$E.$ $coli$ K99 antibody was mixed with 10 μl of the stock $E.$ $coli$ solution and incubated for 30 minutes at room temperature. The 20% stock solution of disodium cromoglycate liquid crystal (50 μl) was added to the microsphere-antibody solution, mixed, and the samples gently centrifuged (3500 g; 5 sec.) to eliminate bubbles. A 60 μl fraction of the mixture was introduced into the glass assay chamber described above.

Comparative Example 8

A commercially available 1.0 μm diameter polycarboxylate microsphere was obtained (Polysciences, Inc, Warrington, Pa.). The polycarboxylate microsphere was coated with a protein that tightly binds microbe specific antibodies. The polycarboxylate microsphere was coated with a goat immunoglobulin that binds all mouse immunoglobulins.

A stock solution of assay microspheres ($10^7/\mu l$) was created by incubating 44 μl of microspheres with 56 μl of BSA for 30 minutes at room temperature. The solution was washed twice with phosphate buffered saline to remove unbound primary antibody.

10 μl of serially diluted polycarboxylate microspheres coated with BSA was mixed with 10 μl of the stock $E.$ $coli$ solution and incubated for 30 minutes at room temperature. The 20% stock solution of the disodium chromoglycate liquid crystal (50 μl) was added to the microsphere-antibody solution, mixed, and the samples gently centrifuged (3500 g; 5 sec.) to eliminate bubbles. A 60 μl fraction of the mixture was introduced into the glass assay chamber described above.

Ligand (bacteria)-bound microsphere aggregates distorted the liquid crystal director to cause local zones of light transmission, which were easily detected.

Figure 4A:
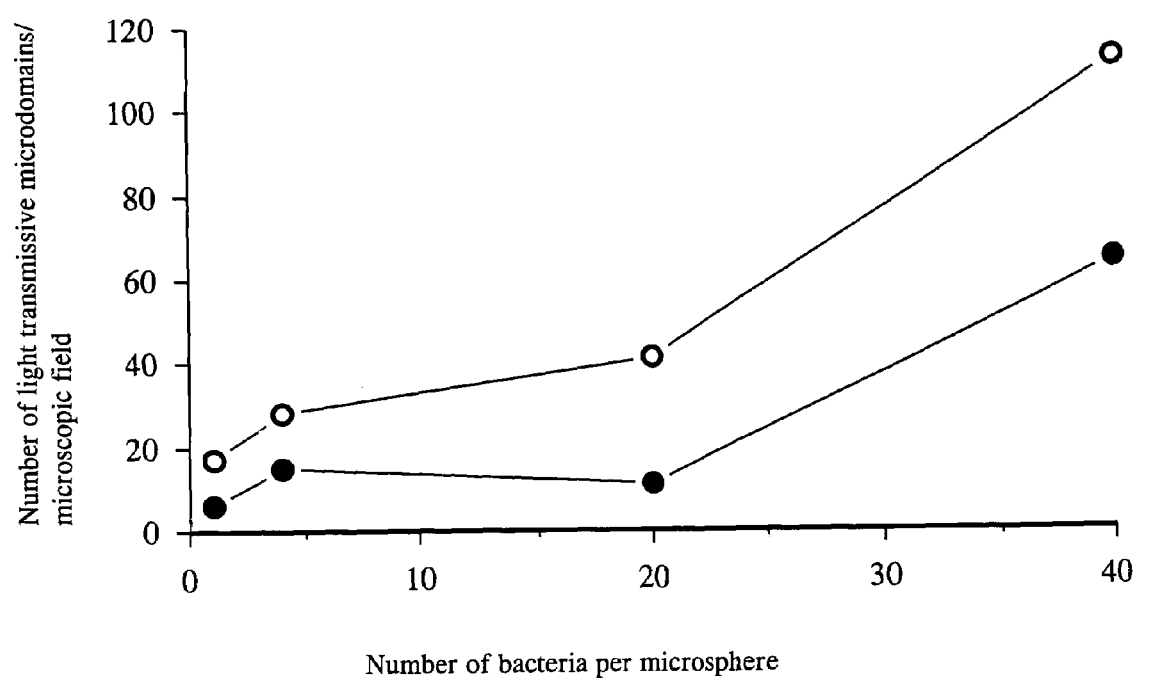

FIG. 4A demonstrates that increasing numbers of light transmissive zones occur in a 14% neutral grey liquid crystalline solution as the ratio of $E.$ $coli$ to polycarboxylate microspheres increases.

Figure 4B:
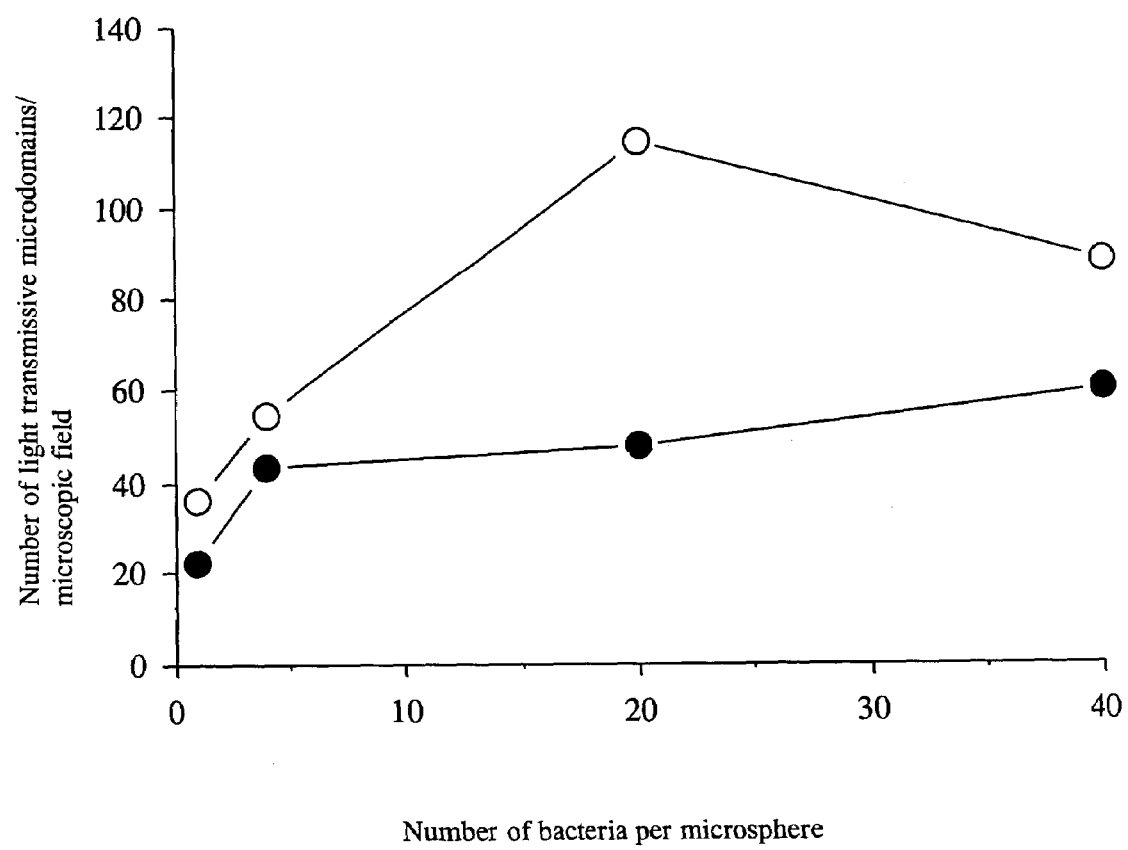
FIG. 4B is a graph showing the number of light transmissive microdomains in the neutral grey liquid crystalline material using (a) polystyrene microspheres coated with anti-*E.coli* antibody and (b) polystyrene microspheres coated with Bovine Serum Albumin. The open circles (○) represent the number of light transmissive microdomains in the neutral grey liquid crystalline material using polystyrene microspheres coated with anti-*E.coli* antibody, and the filled in circles (●)represents the number of light transmissive microdomains in the neutral grey liquid crystalline material using polystyrene microspheres coated with (BSA).

FIG. 4B demonstrates that increasing numbers of light transmissive zones occur in a 14% neutral grey liquid crystalline solution as the ratio of $E.$ $coli$ to polystyrene microspheres increases.

Figure 5A:
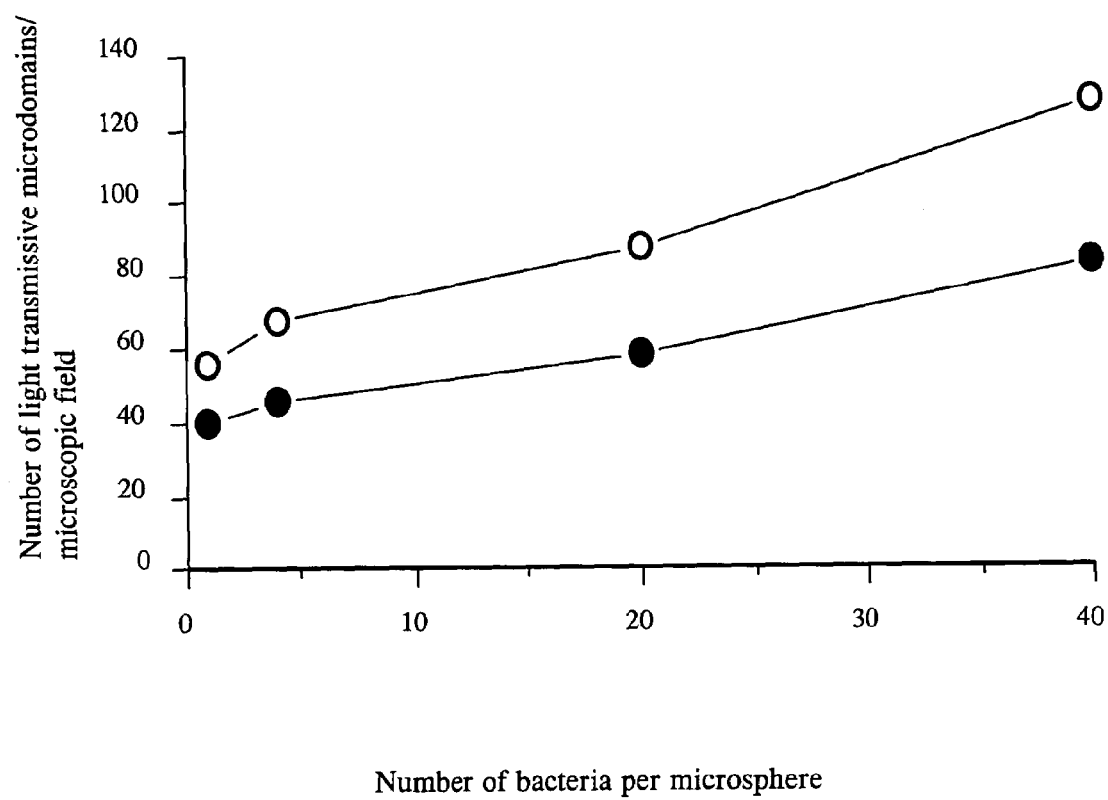
FIG. 5A is a graph showing the number of light transmissive microdomains in the disodium cromoglycate liquid crystalline material using (a) polycarboxylate microspheres coated with anti-E.coli antibody and (b) polycarboxylate microspheres coated with Bovine Serum Albumin. The open circles (○) represent the number of light transmissive microdomains in the disodium cromoglycate liquid crystalline material using polycarboxylate microspheres coated with anti-*E.coli* antibody, and the filled in circles (●)represents the number of light transmissive microdomains in the disodium cromoglycate liquid crystalline material using polycarboxylate microspheres coated with BSA.

FIG. 5A shows that increasing numbers of light transmissive zones occur in a 14% disodium cromoglycate liquid crystalline solution as the ratio of $E.$ $coli$ to polycarboxylate microspheres increases.

Figure 5B:
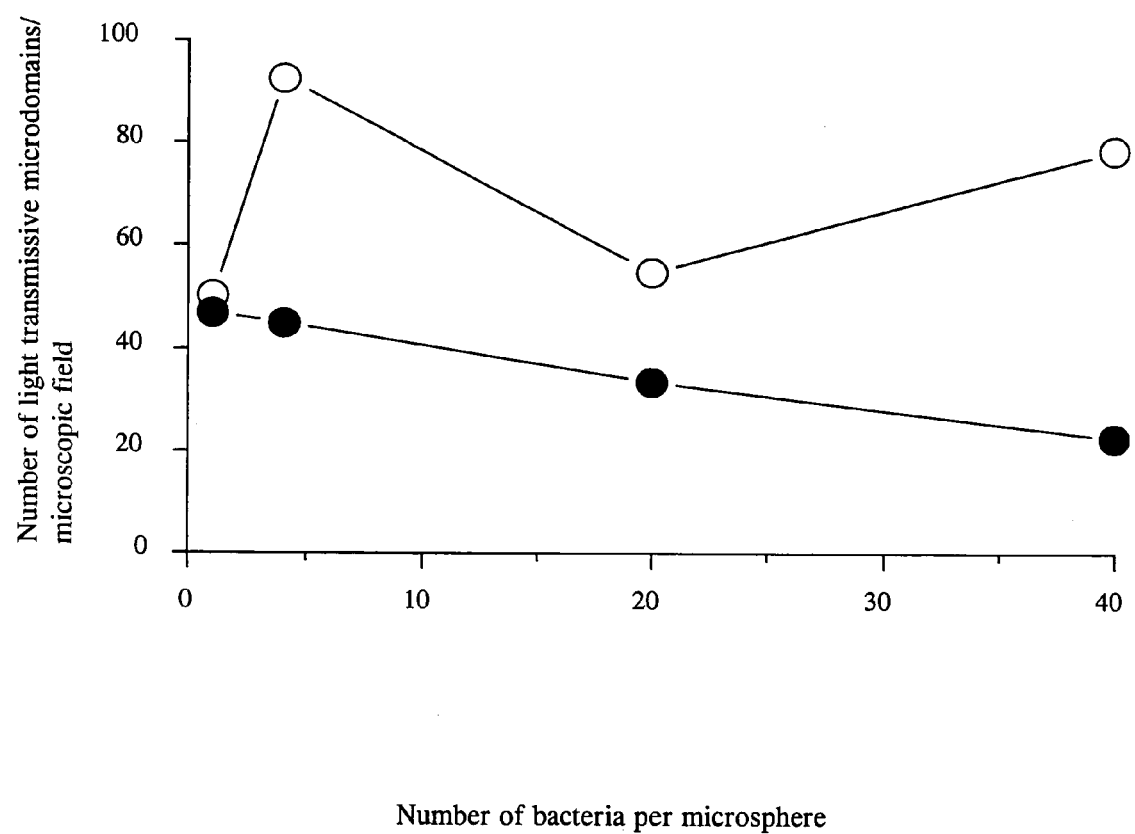
FIG. 5B is a graph showing the number of light transmissive microdomains in the disodium cromoglycate liquid crystalline material using (a) polystyrene microspheres coated with anti-*E.coli* antibody and (b) polystyrene microspheres coated with Bovine Serum Albumin. The open circles (○) represent the number of light transmissive microdomains in the disodium cromoglycate liquid crystalline material using polystyrene microspheres coated with anti-*E.coli* antibody, and the filled in circles (●)represents the number of light transmissive microdomains in the disodium cromoglycate liquid crystalline material using polystyrene microspheres coated with BSA.

FIG. 5B shows that increasing numbers of light transmissive zones occur in a 14% disodium cromoglycate liquid crystalline solution as the ratio of *E. coli* to polystyrene microspheres increases.

Greater light transmission occurred at microsphere to *E. coli* ratios exceeding 1:4. In all experiments, antibody-coated microspheres induced the formation of more light transmissive zones than did the control microspheres coated with Bovine Serum Albumin.

It is to be understood that any variations evident fall within the scope of the claimed invention, and thus the selection of specific receptors, such as antibodies and liquid crystals can be determined without departing from the spirit of the invention herein disclosed and described. It should also be understood that the present invention, while particularly suited for pathogen detection, is intended to include the detection of any ligand. Moreover, the scope of the invention shall include all modifications and variations that may fall within the scope of the attached claims.

We claim:

1. A ligand detection device comprising:

a plurality of particles;

at least one receptor attached to each of said plurality of particles, wherein said at least one receptor is capable of binding at least one ligand to form a receptor-ligand complex; wherein the plurality of particles are positioned and moveable within an mount of a liquid crystalline material, wherein upon formation of said receptor-ligand complex, optical characteristics of said liquid crystalline material are altered to allow detection of said at least one ligand.

2. The device of claim 1, wherein said at least one receptor is attached to the surface of each of said plurality of particles.

3. The device of claim 1, wherein each of the plurality of particles is a porous substrate and said at least one receptor is attached to at least one pore of a porous particle.

4. The device of claim 3, wherein a plurality of receptors are attached to and randomly distributed on the surface and within the pores of said porous particle.

5. The device of claim 1, wherein the liquid crystalline material is selected from the group consisting of thermotropic liquid crystalline material and lyotropic liquid crystalline material.

6. The device of claim 5, wherein the liquid crystalline material is a lyotropic liquid crystalline material.

7. The device of claim 6, wherein the lyotropic liquid crystalline material is a lyotropic chromonic liquid crystalline material.

8. The device of claim 5, wherein the liquid crystalline material is a thermotropic liquid crystalline material.

9. The device of claim 1, wherein the plurality of particles are made from a material selected from the group consisting of polymeric and inorganic materials.

10. The device of claim 9, wherein the polymeric materials are selected from the group consisting of polyions, polyalkenes, polyacrylates, polymethacrylates. polvinyls, polystyrenes, polycarbonates, polyesters, polyurethanes, polyamides, polyimides. polysulfones, polysiloxanes, polysilanes, polyethers, and polycarboxylates.

11. The device of claim 9, wherein the polymeric material is a polystyrene.

12. The device of claim 9, where the plurality of particles are made from an inorganic material selected from the group consisting of glass, silicon, and colloidal gold.

13. The device of claim 12, wherein the inorganic material is glass.

14. The device of claim 1, wherein the particles are substantially spherical.

15. The device of claim 1, wherein said at least one receptor is attached to each of said plurality of particles by at least one mechanism selected from the group consisting of (i) chemical attachment and (ii) physical attachment.

16. The device of claim 15, wherein said chemical attachment is covalent bonding.

17. The device of claim 15, wherein said physical attachment is selected from the group consisting of: hydrophobic interactions and van der Waals interactions.

18. A method for detecting ligands comprising:

providing a device for detecting ligands, said device comprising a plurality of particles; at least one receptor attached to each of said plurality of particles, wherein said at least one receptor is capable of binding to a ligand to form a receptor-ligand complex, and wherein said plurality of particles are positioned within a liquid crystalline material;

contacting a sample with the device, the sample including at least one ligand bindable to the receptor to form the receptor-ligand complex, and detecting the presence of a ligand by means of a change in the optical characteristics of the liquid crystalline material generated by said receptor-ligand complex formation.

19. An amplification device for the detection of ligands comprising:

a plurality of substantially spherical particles;

at least one receptor attached to each of said plurality of substantially spherical particles, wherein said at least one receptor is capable of binding to a ligand to form a receptor-ligand complex; and wherein the particles are positioned within a liquid crystalline material, wherein the optical characteristics of the liquid crystalline material vary to detect the presence of said ligands upon receptor-ligand complex formation within the liquid crystalline material.

20. A device for detection of a ligand comprising:

an amount of liquid crystalline material, the liquid crystalline material having initial optical transmission characteristics;

a plurality of particles positioned in the amount of liquid crystalline material so as to be moveable therein;

at least one ligand receptor associated with the plurality of particles, the ligand receptor capable of attaching to a ligand, wherein upon attachment of a ligand to the receptor, the initial optical characteristics of the liquid crystalline material are altered; and a detector for detecting a change in the initial optical characteristics of the liquid crystalline material to determine the presence of a ligand.

21. A method for detecting a ligand comprising the steps of:

providing an amount of liquid crystalline material having initial optical characteristics;

positioning a plurality of particles having at least one ligand receptor associated therewith, it the liquid crystalline material so as to be moveable throughout the liquid crystalline material; and detecting a change from the initial optical characteristics in the liquid crystalline material indicating attachment of at least one ligand to the receptor and the presence of the ligand thereby.

* * * * *

UNITED STATES PATENT AND TRADEMARK OFFICE
CERTIFICATE OF CORRECTION

PATENT NO. : 7,160,736 B2
APPLICATION NO. : 10/726134
DATED : January 9, 2007
INVENTOR(S) : Gary D. Niehaus et al.

It is certified that error appears in the above-identified patent and that said Letters Patent is hereby corrected as shown below:

Page 1, under "Inventors," add --Kathleen J. Doane, Ravenna, OH (US)--

Col. 23, line 27 replace "mount" with --amount--.

Col. 23, line 57 replace "polvinyls" with --polyvinyls--.

Signed and Sealed this

Twenty-fifth Day of March, 2008

JON W. DUDAS
*Director of the United States Patent and Trademark Office*